United States Patent
Zilberman

(10) Patent No.: US 7,834,221 B2
(45) Date of Patent: Nov. 16, 2010

(54) PROCESS FOR THE PREPARATION OF TETRABROMOBISPHENOL A

(75) Inventor: Joseph Zilberman, Haifa (IL)

(73) Assignee: Bromine Compounds Ltd., Be'er Sheva (IL)

( * ) Notice: Subject to any disclaimer, the term of this patent is extended or adjusted under 35 U.S.C. 154(b) by 4 days.

(21) Appl. No.: 11/988,274

(22) PCT Filed: Jul. 3, 2006

(86) PCT No.: PCT/IL2006/000771

§ 371 (c)(1),
(2), (4) Date: May 2, 2009

(87) PCT Pub. No.: WO2007/007315

PCT Pub. Date: Jan. 18, 2007

(65) Prior Publication Data

US 2010/0010274 A1    Jan. 14, 2010

(51) Int. Cl.
*C07C 37/62* (2006.01)

(52) U.S. Cl. ........................ 568/726; 568/779

(58) Field of Classification Search ........ None
See application file for complete search history.

(56) References Cited

U.S. PATENT DOCUMENTS

| | | | |
|---|---|---|---|
| 3,546,302 | A | 12/1970 | Asadoriam et al. |
| 3,929,907 | A | 12/1975 | Janzon et al. |
| 5,068,463 | A | 11/1991 | Walter |
| 5,475,153 | A | 12/1995 | Armstrong |
| 5,847,232 | A | 12/1998 | McKinnie |
| 6,245,950 | B1 | 6/2001 | Kantam et al. |
| 6,365,786 | B1 | 4/2002 | Ramachandraiah et al. |

FOREIGN PATENT DOCUMENTS

| | | |
|---|---|---|
| DE | 26 13 969 | 10/1977 |
| DE | 1590 66 | 2/1983 |
| DE | 211 781 | 7/1984 |
| EP | 1 149 817 A1 | 10/2001 |
| IL | 64410 | 11/1981 |
| JP | 7-33700 | 2/1995 |
| RU | 2 034 823 | 5/1995 |
| RU | 2 034 823 C1 | 5/1995 |
| WO | 96/33964 | 10/1996 |

OTHER PUBLICATIONS

International Search Report mailed Nov. 16, 2007.
Written Opinion of the International Searching Authority mailed Nov. 16, 2007.
Supplementary European Search Report issued for European Patent Application No. EP 06 76 6112, dated Feb. 26, 2010.
I.M. Lazarev, et al. Oxidative Bromination of Bisphenols. Synthesis of 4,4'-Isopropylidenebis(2,6-dibromophenol), Russian Journal of Organic Chemistry, vol. 36, No. 12, 2000, pp. 1758-1759.
"Brominated Phenols Prodn.—By Reacting Phenols With Bromien in 2-Phase System Contg. alkali Bromate and Electrolytically Oxidising Resulting Bromide Back to Bromate", Chem Fab Kalk GMBH, Jun. 3, 2008, 4 pages.
Japanese Application JP 07-33700 (1995), 8 pages.
"The Study of the Green Technology of Tetrabromobisphenol A", Fine Chemicals, vol. 18, No. 11, Nov. 2001 (with a partial translation).

*Primary Examiner*—Brian J Davis
(74) *Attorney, Agent, or Firm*—Nixon & Vanderhye P.C.

(57) ABSTRACT

A process for preparing tetrabromobisphenol A, which comprises: i) reacting bisphenol A and bromine in dichloromethane in the presence of aqueous hydrogen peroxide at a temperature in the range of room temperature to the reflux temperature, wherein said dichloromethane is present in an amount sufficient for substantially dissolving brominated derivatives of said bisphenol A formed thereby, ii) separating the substantially solid-free reaction mixture obtained in step i) into aqueous and organic phases, precipitating tetrabromobisphenol A from the organic phase and isolating said precipitated tetrabromobisphenol A from said organic phase.

18 Claims, 1 Drawing Sheet

PROCESS FOR THE PREPARATION OF TETRABROMOBISPHENOL A

This application is the U.S. national phase of International Application No. PCT/IL2006/000771, filed 3 Jul. 2006, which designated the U.S. and claims priority to Israel Application No. 169592 filed 7 Jul. 2005, the entire contents of each of which are hereby incorporated by reference.

4,4'-isopropylidene-bis(2,6-dibromophenol), which is also known as tetrabromobisphenol A (hereinafter sometimes abbreviated TBBA), is used both as a reactive flame retardant in the manufacture of epoxy, phenolic and polycarbonate resins, and as an additive flame retardant in acrylonitrile-butadiene-styrene systems. For these applications, it is generally necessary to use high quality tetrabromobisphenol A. The product must be substantially free from reaction by-products and hydrolysable bromine, have good color characteristics and a very low ionic bromide content. In some applications it is also necessary to use a free-flowing powder with a specific particle size and particle size distribution.

The preparation of tetrabromobisphenol A is generally based on the bromination of bisphenol A. Several processes were described in the art in this regard, suggesting various reaction conditions for improving the aforementioned general reaction scheme.

U.S. Pat. No. 5,475,153 and WO 96/33964 disclose the bromination of bisphenol A using an aqueous lower alcohol as a solvent, specifically addressing the problem of the undesired formation of methyl bromide and ethyl bromide by-products. WO 96/33964 also describes a continuous mode of operation for carrying out the bromination of bisphenol A.

The bromination of bisphenol A using water-immiscible organic solvents was also disclosed in the art (e.g., U.S. Pat. Nos. 3,546,302, 3,929,907, 6,365,786, Ger. Offen. 2613969, Ger. East 159066, Ger. East 211781, Israeli patent no. 64410, RU 2034823 and JP 7-033700A). The processes described in the aforementioned publications are carried out in the presence of water, such that the reaction mixture consists of two liquid phases, that is, an organic phase and an aqueous phase. The use of hydrogen peroxide, for the purpose of in-situ recycling the hydrogen bromide formed in the bromination reaction, to afford molecular bromine available for further brominating the bisphenol-A nucleus, has also been proposed in said publications.

Tetrabromobisphenol A is typically contaminated by various impurities, such as brominated phenols and color-causing chemical substances. For example, an undesired decomposition by-product associated with the bromination of bisphenol A in the aforementioned two-phase system, which comprises water-immiscible organic solvent and an aqueous phase, is tribromophenol.

The present invention relates to a process for the bromination of bisphenol A in dichloromethane, in the presence of water and an oxidizer, which process affords highly pure crystalline tetrabromobisphenol A in the form of a white, free flowing powder, contaminated by only negligible amounts of organic impurities. Most advantageously, the process provided by the present invention is carried out in a continuous mode of operation.

The present invention is primarily directed to a process for preparing tetrabromobisphenol A, which comprises:

i) reacting bisphenol A and bromine in dichloromethane in the presence of aqueous hydrogen peroxide at a temperature in the range of room temperature to the reflux temperature, wherein said dichloromethane is present in an amount sufficient for substantially dissolving brominated derivatives of said bisphenol A formed thereby, ii) separating the substantially solid-free reaction mixture obtained in step i) into aqueous and organic phases, precipitating tetrabromobisphenol A from the organic phase and isolating said precipitated tetrabromobisphenol A from said organic phase.

In general terms, the process according to the present invention comprises a bromination reaction and a subsequent work-up treatment for recovering the product in a solid form, defined by steps i) and ii) above, respectively.

As used herein, the term "brominated derivatives of bisphenol A" refers to one or more of the following bromination products: di-, tri-, and tetrabromobisphenol A. The process according to the present invention requires the dichloromethane solvent to be used in a sufficiently large quantity such that the brominated derivatives of bisphenol A formed in the course of the bromination reaction are substantially dissolved in said dichloromethane. The terms "substantially dissolving brominated derivatives of bisphenol A" and "substantially solid-free reaction mixture" refer to the fact that said brominated derivatives of bisphenol A are either fully dissolved in the dichloromethane or possibly suspended therein, wherein the weight concentration of said suspended brominated derivatives of bisphenol A in the organic phase is not greater than 3%, and more preferably not greater than 1% (w/w).

It has been found that carrying out the bromination reaction under the conditions of the invention, with essentially complete dissolution of the brominated derivatives of bisphenol A in dichloromethane, and, preferably, with the volumetric ratio of the organic phase to the aqueous phase in the reaction mixture being not less than 6:1, and more preferably not less than 10:1, affords highly pure product having the desired particle size distribution and good flowability, and minimizes the formation of undesired decomposition reaction products, such as tribromophenol.

The bromination reaction according to the present invention is carried out at a temperature in the range of room temperature to the reflux temperature of dichloromethane, and preferably at a temperature in the range of 30° C. to the reflux temperature of said solvent, and more preferably in the range of 35° C. to the reflux temperature of said solvent, and most preferably at the reflux temperature of dichloromethane (38-41° C. at atmospheric pressure). It should be noted that the reaction is generally carried out under atmospheric pressure. However, it is possible, if desired, to carry out the bromination reaction under sub-atmospheric pressure or under excess pressure, in which cases, of course, the reflux temperature of the system will be different from the specific value indicated above.

The amount of dichloromethane that is used according to the process of the present invention needs to be sufficiently large to substantially dissolve the brominated derivatives of bisphenol A formed, preventing spontaneous precipitation thereof from the reaction mixture, whereupon various impurities present in the reaction mixture may be entrapped by the precipitated material. This feature of the invention is particularly important for running the process in a continuous mode, as will be discussed in more detail below. Quantitatively, it has been observed that it is especially preferred to use dichloromethane in an amount such that the calculated concentration of tetrabromobisphenol A in the organic phase upon completion of the bromination reaction is about 15-25% by weight, and preferably about 20-23% by weight (these calculated concentrations are based on the assumption that the bisphenol A used as a starting material is completely converted into tetrabromobisphenol A). The bisphenol A can be added to the reaction vessel either in a molten form, or as a solid using a suitable solids addition feeder, or as a slurry in dichloromethane, with the latter option being preferable. When the bromination reaction is carried out according to the preferred conditions indicated above (namely, at the reflux temperature under normal pressure), then the content of the bisphenol A starting material in the aforementioned slurry is most suitably in the range of 7.0-12.3% (w/w). This concentration of the bisphenol A starting material yields the desired concentration of tetrabromobisphenol A in the organic phase of the final reaction mixture (namely, of about 15-25% (w/w) tetrabromobisphenol A in said final organic phase).

The total amount of bromine required for the complete tetrabromination is generally 2 mole per mole of BPA, taking into consideration that all the HBr formed is quantitatively oxidized into bromine by the oxidizer present in the reaction vessel. It is preferred to use a slight stoichiometric excess of bromine, that is, slightly more than 2 mole of bromine per mole bisphenol A, and more preferably between 2.05 to 2.1 mole of bromine per mole bisphenol A.

The oxidizing agent used according to the present invention, hydrogen peroxide, is provided in the form of an aqueous solution the concentration of which is typically in the range of 30 to 70% by weight, and preferably about 50% by weight. The hydrogen peroxide is used in a sufficient amount to convert substantially all the hydrogen bromide formed in the reaction to bromine, the preferred amount of hydrogen peroxide being between 2 to 2.1 mole per mole bisphenol A, and more preferably between 2.05 to 2.1 mole per mole bisphenol A.

The volumetric ratio between the organic and aqueous phases is preferably not less than 6:1, and most suitably in the range of 6:1 to 26:1, according to the concentrations of the bisphenol A starting material and the oxidizer in the dichloromethane and in the $H_2O_2$ aqueous solution used, respectively. For example, when the concentration of the aqueous solution of hydrogen peroxide used is about 50% by weight, and the concentration of bisphenol A in dichloromethane is in the range of 7 to 12.3% w/w (corresponding to a desired concentration of 15 to 25% (w/w) tetrabromobisphenol A in the final reaction mixture), then the volumetric ratio between the organic and aqueous phases should most preferably be in the range of 10:1 to 18:1.

When the reaction is carried out in a batch mode, the various reactants and reagents may be introduced into the reaction vessel according to any desired order. It is preferred, however, to carry out the reaction under conditions wherein the oxidizer is present in a molar excess relative to bromine. Thus, the reaction vessel is loaded at an ambient temperature with bisphenol A, the dichloromethane solvent and a portion of the contemplated amount of aqueous hydrogen peroxide, followed by a gradual addition into said reaction vessel of the remaining amount of said oxidizer concurrently with the gradual addition of bromine, or more preferably, a solution of bromine in dichloromethane. The gradual addition of the oxidizer and bromine into the reaction vessel may be carried out either in a portion-wise manner or most preferably continuously, at constant rates, which rates may be readily adjusted by the skilled artisan, in accordance with various process parameters, such as the efficacy of the cooling system, etc. For example, bromine may be added into the reaction vessel at a constant rate over 10 to 120 minutes. Under the aforementioned conditions, hydrogen peroxide is present in the reaction mixture in a molar excess in respect to bromine.

Typical reaction times for the batch bromination reaction according to the invention may vary between 45 to 140 min. It should be understood, however, that the aforementioned reaction durations may be shorter or longer, according to the reaction scale, the rate of heat removal, etc.

The bromination reaction according to the process of the present invention may be carried out either in a batch mode or in a combined batch-continuous mode (e.g., initiating the bromination reaction in a batch reactor and completing the same in a continuous mode). It is particularly advantageous to run the bromination reaction according to the present invention in a continuous mode.

The reflux conditions employed in the course of the bromination reaction ensure a sufficiently rapid reaction rate while the large quantity of the organic solvent present in the reaction mixture suppresses the precipitation of the reaction products, thus facilitating the continuous withdrawal and feeding of the liquid, solid-free reaction mass. It has been unexpectedly found that the bromination reaction according to the present invention does not exhibit any considerable formation of by-products, the reaction mixture obtained being essentially free from tribromophenol. As used herein, by the term "essentially free from tribromophenol" is meant that the tribromophenol content in the final bromination mixture is less than 0.6% (GC area %) relative to the TBBA.

Thus, according to a particularly preferred embodiment of the invention, there is provided a process, which comprises:

i) continuously feeding into a first reaction volume bisphenol A and bromine, reacting the same in dichloromethane in the presence of aqueous hydrogen peroxide at a temperature in the range of room temperature to the reflux temperature, wherein said dichloromethane is used in an amount sufficient for substantially dissolving brominated derivatives of said bisphenol A formed thereby, continuously removing from said first reaction volume substantially solid-free reaction mass, contacting, in a second reaction volume, said reaction mass with bromine, to form a substantially solid-free final reaction mixture the predominate product of which is tetrabromobisphenol A;

ii) separating said substantially solid-free final reaction mixture into aqueous and organic phases, precipitating said tetrabromobisphenol A from said organic phase and isolating the precipitated tetrabromobisphenol A from said organic phase.

The term "predominate product", as used herein, means that the product obtained in the final bromination mixture preferably contains not less than 95%, and more preferably not less than 97% tetrabromobisphenol A (area percent obtained by GC analysis).

By the term "reaction volume", as used herein in respect to the continuous process, is meant a volume into which reactants are continuously introduced, and from which products are withdrawn, maintaining within said volume an essentially constant amount of the reaction mixture. According to the process of the present invention, the bromination reaction is initiated in a first reaction volume into which the bisphenol A starting material and a suitable amount of bromine are continuously fed and reacted in dichloromethane in the presence of hydrogen peroxide, to form a substantially solid-free reaction mass containing a mixture of brominated derivatives of bisphenol A, which mixture preferably comprises not less than 55%, and more preferably not less than 65%, and most preferably not less than 75% tetrabromobisphenol A (GC area %), and in a second reaction volume, into which the aforementioned solid-free reaction mass is being continuously fed together with suitable amounts of bromine, to complete the desired tetrabromination.

Typically, each of said first and second reaction volumes is provided in a distinct reaction vessel, which is most suitably in the form of a continuously stirred reactor. It should be understood, however, that the first and second reaction volumes according to the present invention may be optionally provided within a single reaction vessel (for example, in a tubular plug flow type reactor).

FIG. 1 schematically illustrates a particularly preferred arrangement of reactors for carrying out the continuous process according to the invention. According to the preferred embodiment shown in FIG. 1, the first reaction volume 1 is provided in a continuously stirred reactor 11, into which bisphenol A, bromine, aqueous hydrogen peroxide solution and dichloromethane are continuously charged, and from which a reaction mass comprising brominated derivatives of bisphenol A is continuously removed. The second reaction volume 2 is most preferably provided within two or more, and most suitably three, consecutively arranged continuously stirred reactors (designated 21, 22, and 23) or, alternatively, within a tubular plug flow type reactor (not shown). Suitable amounts of bromine are being continuously fed to the first of said consecutively arranged continuously stirred reactors 21, while the reaction mass exiting reactor 11, which reaction mass comprises brominated derivatives of bisphenol-A, is being continuously fed into said first reactor 21, whereby the desired tetrabromination is gradually accomplished in said second reaction volume provided within reactors 21, 22 and 23.

In order to effectively introduce the reactants into reactor 11, it is particularly preferred to prepare a slurry of bisphenol A in dichloromethane in a separate stirred vessel (not shown in the FIGURE), following which said slurry is supplied from said vessel to the continuous reactor 11 by means of gravity flow or a slurry feeding pump. This method enables the bisphenol A to be fed to any desired point in the continuous reactor 11 through a dip pipe, if desired. The preferred weight ratio between bisphenol A and the dichloromethane solvent, which was indicated hereinabove in relation to the general process scheme, applies also in case that the bromination reaction is run in a continuous mode, as shown in FIG. 1.

As indicated hereinabove, it is preferred to use slightly more than 2 mole of bromine per mole bisphenol A, and more preferably between 2.05 to 2.1 mole. As may be appreciated in the light of the foregoing description, the total amount of bromine used for the bromination reaction is divided between the first reaction volume and the second reaction volume, as will now be explained in more detail.

The amount of bromine charged into reactor 11 is preferably 80-95% of the total bromine required for the complete tetrabromination, and more preferably about 85-93%. The bromine is fed into reactor 11 simultaneously with the bisphenol A feed, either in the form of a pure liquid bromine, or as a solution in dichloromethane. It has been observed that the introduction of at least 80% of the total amount of bromine into reactor 11 facilitates the formation of a mixture of brominated derivatives of bisphenol A which are capable of being completely dissolved in the organic phase, thus eliminating the precipitation of solids in the reaction mass within the reactor 11, and therefore in the outlet of said reactor. Specifically, under the aforementioned conditions, the brominated derivatives of bisphenol A are contaminated by only negligible amounts of the undesired decomposition by-products, for example, the amount of tribromophenol is most preferably less than 0.2% by weight relative to the total amount of said brominated derivatives of bisphenol A.

The oxidizing agent used according to the present invention, hydrogen peroxide, is fed into reactor 11 concurrently with the bromine feed, in the form of an aqueous solution. The hydrogen peroxide can be added into the reactor 11 in an amount equivalent to the amount of bromine used, with the rest being added into the second reaction volume for the completion of the bromination. It is preferable, however, from the operational point of view to supply all the hydrogen peroxide in the first reaction volume, namely, in reactor 11.

The contents of the reactor 11 are held at a temperature in the range of 35° C. to reflux temperature, and most preferably around the reflux temperature.

The process according to the present invention comprises two very exothermic reactions—bromination and oxidation of hydrogen bromide, as well as exothermic absorption of HBr by the aqueous phase. The bromination is preferably performed at reflux using a reflux-condenser, allowing heat removal by means of solvent vaporization which is more efficient than cooling the reaction mass through a heat exchanger.

The residence time in the reactor 11 is mainly dictated by the efficiency of the cooling system. The feed rates of the input and the discharge from the reactor are adjusted so that the residence time is about 0.5-4 hours, and preferably 0.6-1.5 hours. Reactor residence time, as used herein, is the volume of the reactor contents divided by the flow rate at which the reaction mass is removed from the reactor.

The reaction mass that is continuously removed from reactor 11 is a two-phase system, consisting of the organic phase containing the brominated derivatives of bisphenol A dissolved in dichloromethane and the aqueous phase containing mainly the excess hydrogen peroxide. The withdrawn reaction mass is fed continuously into the first reactor 21 of the consecutively arranged reactors 21, 22, 23, while bromine is also being continuously fed into said reactor 21 to allow the aforementioned brominated derivatives of bisphenol A that are present in said reaction mass to accomplish the desired tetrabromination, affording a solid-free reaction mixture comprising the organic phase containing the desired tetrabromobisphenol A as the predominant product, and the aqueous phase.

As indicated above, the remaining 5-20% of the total bromine required for the complete tetrabromination is fed into reactor 21. The temperature in the successively arranged reactors 21, 22 and 23 is in the range of 35 to 40° C., and preferably from 38 to 40° C., and most preferably at the reflux temperature. The total volume of the reactors 21, 22 and 23 is adjusted so that the total residence time is sufficient to complete the tetrabromination. The total residence time in said reactors is about 10-30 min, and preferably 10-20 min.

It has been found that the formation of the unwanted by-products becomes considerable at the end of the bromination when the unreacted bromine does not have enough ortho-positions for the ar-bromination and as a result attacks at the ipso-position of the tetrabromobisphenol A leading to the formation of tribromophenol and 4-isopropylidene-2,6-dibromophenol as the primary tetrabromobisphenol A decomposition products. Thus, on the one hand, the presence of excess bromine at the end of the bromination reaction assures that the necessary degree of bromination has been achieved within the acceptable residence time, while on the other hand, said excess bromine may lead to the decomposition of the tetrabromobisphenol A.

The unreacted bromine concentration in the organic phase of the final reaction mixture is an indicator of both the degree of bromination and the level of undesired side reactions, namely, the decomposition of tetrabromobisphenol A. It was found experimentally that the optimal unreacted bromine concentrations in the final organic phase are in the range of about 1,000 to about 10,000 ppm, and preferably in the range of about 2,000 to about 6,000 ppm (the ppm values are based on the weight of the organic phase of the final reaction mixture). These concentrations indicate that the desired degree of bromination is achieved within the chosen process parameters of this invention, and with the formation of the unwanted by-products being sufficiently suppressed.

Unreacted bromine concentrations below about 1000 ppm in the final reaction mixture indicate that the desired tetrabromination reaction does not reach completion in the second reaction volume. Unreacted bromine concentrations above about 10000 ppm in the final reaction mixture point to a rapid build up of by-products to amounts preventing the obtainment of a high purity tetrabromobisphenol A in high yields.

The desired level of unreacted bromine is maintained by measuring its concentration at the outlet of the last reactor of the consecutively arranged plurality of reactors in which the second reaction volume is provided (namely, reactor 23 in FIG. 1), and adjusting the bromine feed to the first reactor of said plurality of reactors (namely, reactor 21 in FIG. 1) to the desired concentration of unreacted bromine in the final reaction mass. The color of the reaction mass may be used to measure the bromine concentrations.

Having completed the bromination reaction (either in the batch mode or in the continuous mode), the final reaction mixture is treated with a reducing agent which is most suitably selected from the group consisting of sodium bisulfite, sodium sulfite, ammonium hydroxide and hydrazine.

It is particularly preferred to use a sufficiently large ratio of dichloromethane to bisphenol A in the bromination reaction, to the extent that the spontaneous precipitation of tetrabromobisphenol A is substantially suppressed not only during the bromination reaction itself, but also in the course of the following work-up treatment of the final reaction mixture, at least up until the separation of the organic phase from the aqueous phase. Tetrabromobisphenol A obtained by spontaneous precipitation from the organic phase during the bromination reaction entraps organic and inorganic impurities. It contains increased amounts of organic impurities which may worsen its color characteristics as well as increased amounts of bromides. Furthermore, it has been observed that the quality of tetrabromobisphenol A which spontaneously precipitates from the final reaction mixture before the accomplishment of the phase separation is inferior, in terms of particle size distribution and flowability characteristics, in comparison with the product obtained upon precipitation from the separated organic phase, especially after said separated organic phase has been also thoroughly washed with water. The preferred weight ratio indicated hereinbefore between the bisphenol A starting material and dichloromethane used for the bromination reaction (a concentration of 7 to 12.3% w/w of the said starting material in said solvent) is sufficient for adequately suppressing the spontaneous precipitation of the product from the crude reaction mixture at least up until the crude reaction mixture is separated into its organic and aqueous phases.

Accordingly, upon reduction of the unreacted bromine and traces of hydrogen peroxide, as explained hereinabove, the two-phase mixture consisting of an organic phase containing the tetrabromobisphenol A dissolved therein and an aqueous phase containing inorganic salts is further treated in the batch mode or in the continuous mode to recover the product therefrom. The two-phase mixture is separated and the substantially solid-free organic phase is washed with water. A stirred reactor is employed for the washing which is carried out in the batch mode. For continuous washing, counter current extraction using a cascade of continuously stirred reactors or a Karr column can be employed.

The washing of the organic phase (containing the product dissolved therein) with water is useful for reducing the content of the remaining bromides and sulfates to the desired minimal level, and thus to avoid their precipitation during the product crystallization which would reduce the product quality. The washing is carried out to the pH value required by the corrosion resistance of the equipment used for the work up stages of the process. In general, it is preferred to perform two successive equal water washings of the organic phase, while the total amount of water used is at least one volume per volume of the organic phase.

The washed organic phase is in the form of a solution containing substantially all the tetrabromobisphenol A as a solute. The process of the present invention requires "precipitating" the tetrabromobisphenol A from the washed organic phase. The precipitation is preferably crystallization, aimed at obtaining a highly pure product with the desired particle size distribution. The crystallization is carried out according to generally known methods, such as flash cooling crystallization and evaporative crystallization. Most suitably, the crystallization of the product from the dichloromethane solution comprises concentrating said solution by evaporating a portion of the solvent therefrom, to form a suspension wherein the concentration of the tetrabromobisphenol A in said suspension is most preferably in the range of 60-70% by weight, followed by cooling the suspension to a temperature in the range of 5 to 10° C.

The separation of the crystals from the liquid phase is performed by using conventional solid-liquid separation devices such as filters and centrifuges. The product cake is washed with cooled dichloromethane before removal from the filter or centrifuge. The filtrate may be treated similarly to the primary organic phase, to recover additional crops of the product therefrom.

The tetrabromobisphenol A product obtained by the process of this invention has a melting point above 180° C., and preferably has a purity of at least 99% (gas chromatography area), is a white, free-flowing powder with a specific particle size and particle size distribution, has an ionic bromide content of less than 10 ppm, APHA color numbers of a 50% solution in acetone less than 30 and of a 20% solution in 1.5 N sodium hydroxide of less than 70. The process yields are higher than 95%, with respect to the amount of bisphenol A starting material used.

A number of illustrative and non-limitative embodiments of the invention will now be described, with reference to the examples below.

EXAMPLES

Figure 1:
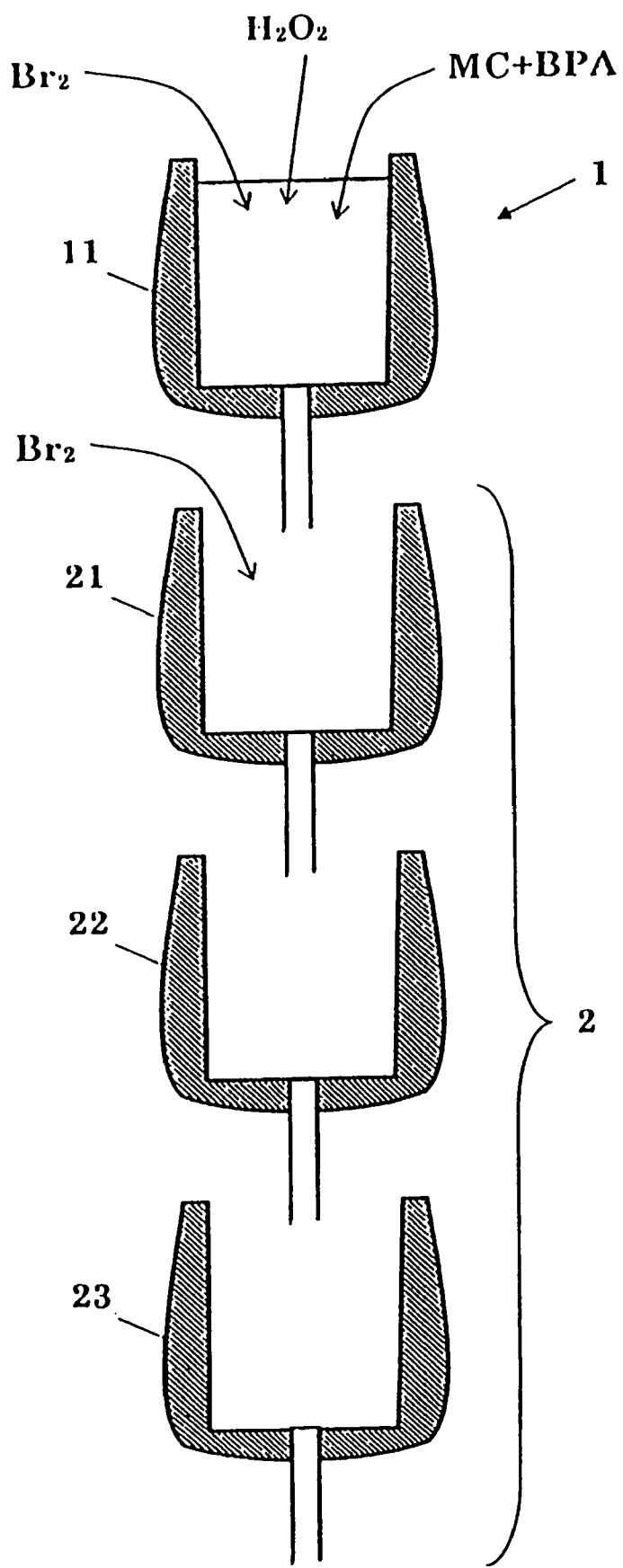
FIG. 1 illustrates a preferred arrangement of reactors for carrying out the continuous process of the invention.

In the Examples, unless otherwise specified, all the percentages used for the characterization of solutes and solid products, are area percent values obtained by gas chromatography (GC) analysis.

The following abbreviations are used in the examples:

BPA—bisphenol A

MC—dichloromethane

TBBA—tetrabromobisphenol A

TBP—tribromophenol

PSD—Particle size distribution

GC analyses of the reaction mixtures and the final products were conducted on an HP 5890 Series II apparatus. Oven: Initial temperature 130° C., hold 0.5 min, then raised to 300° C. at 30° C./min. Injector: 250° C. Detector (FID): 300° C. Column: capillary, Rtx 1, 15 m×0.25 mm (ID)×0.25 µm, packed with crossbonded 100% dimethyl polysiloxane. Split ratio: 1:100. Flow ($N_2$): 1 ml/min.

Quantitative HPLC analyses of TBP and TBBA in the reaction mixtures were conducted on a Varian 9010 instrument. A weighed sample of the organic phase (2-3 g) underwent stripping at room temperature under vacuum over a period of 7 min to completely remove MC. The solid residue was weighed and dissolved in a known amount of acetonitrile (5-7 g). The acetonitrile solutions were analyzed quantitatively. The column used was a 5 micron Kromasil KR100-5 C18 (25 cm×4.6 mm). HPLC conditions: flow rate 1.5 ml/min, detection: $\lambda$=230 nm; eluent: 80% acetonitrile and 20% water with 0.1% acetic acid.

The particle size distribution (PSD) of TBBA was measured in water with the addition of 1% w/w surfactant, Atlox, by the Malvern laser diffraction method on a Mastersizer 2000.

The quantitative determination of inorganic bromide content was performed by argentometric titration in acetone.

The color (APHA) of TBBA solution in acetone (50%) is determined using a photometer or a comparator for APHA (Hazen) units.

The color (APHA) of TBBA solution in 1.5N NaOH (20%) is determined using a photometer or a comparator for APHA (Hazen) units.

Example 1

Preparation of Tetrabromobisphenol A in a Continuous Mode i) General Description of the System The system is described with reference to the arrangement shown in FIG. 1.

The First Reaction Volume (in which the Bromination was Initiated)

The reaction system consisted of a stirred vessel for preparing a slurry of BPA in dichloromethane, and a reactor (designated by numeral 11 in FIG. 1), equipped with a mechanical stirrer, a thermometer and a reflux condenser. The BPA slurry, bromine (neat or as a solution in dichloromethane) and aqueous hydrogen peroxide were fed into the reactor continuously and simultaneously by means of peristaltic pumps. Concurrent with the addition of BPA, bromine and hydrogen peroxide, a steady stream of the reaction mixture flowed down to the following reactor (numeral 21 in FIG. 1), by gravity flow in such a way that the reaction volume in reactor 11 remained constant.

The Second Reaction Volume (in which the Bromination was Completed)

The second reaction volume was provided within a cascade of three reactors (designated 21, 22 and 23 in FIG. 1), each equipped with a mechanical stirrer, a thermometer and a reflux condenser. The reaction mass exiting reactor 11 and the rest of the bromine needed for completion of the bromination were fed continuously into the first reactor 21 in the cascade. The reaction solution flowed down from one reactor to the next in the cascade by gravity flow. Concurrent with the feeding of partially brominated material from the reactor 11 and bromine, a steady stream of the final bromination mixture exiting the last reactor 23 of the aforementioned cascade of reactors (21, 22 and 23) flowed down to a stirred vessel at such a flow rate that the reaction volume in said cascade of reactors remained constant. A reducing agent solution was fed continuously to the stirred vessel to neutralize the unreacted bromine and traces of hydrogen peroxide.

ii) Start-Up

To start the continuous operation, a mixture of brominated derivatives of bisphenol A, having a composition that corresponds to that of the effluent exiting the first reaction zone was prepared in a batch mode.

806 g of a pre-prepared 11.4% (w/w) slurry of BPA in dichloromethane and 54.3 g aqueous 52% hydrogen peroxide were charged into a 2 l reactor equipped with a mechanical stirrer, a thermometer and a reflux condenser. 123 g bromine was added to the reactor contents over 1 h under reflux conditions. The reactions mixture was free from solids. The solute contained 0.4% dibromobisphenol A, 25% tribromobisphenol A and 74.2% TBBA. About 650 ml of this mixture of brominated derivatives of bisphenol A so prepared was charged to reactor 11. The rest was charged to reactors 21 and 22.

iii) Continuous Operation

Feeding of the pre-prepared 11.4% (w/w) slurry of BPA in dichloromethane, aq. 52% $H_2O_2$ and bromine was begun at constant rates of 11.5, 0.78 and 1.75 g/min, respectively. The molar ratios of $Br_2$ to BPA and of $H_2O_2$ to BPA (i.e. the molar quantities of $Br_2$ and $H_2O_2$ added to reactor 11 per unit time divided by the molar quantity of BPA added per unit time) were 1.9 and 2.07, respectively. Concurrent with the start of the constant feeds of the reagents, a constant take-off was begun to maintain the reaction volume at 650 ml. The bromination mixture was maintained at reflux (39-41° C.) by the reaction heat.

The average residence time in reactor 11 was about 60 min. The effluent from reactor 11 stabilized at a solute composition of <0.1% tribromophenol, 0.5-1% dibromobisphenol A, 22-25% tribromobisphenol A and 74-77% TBBA.

The effluent from reactor 11 was fed to the reactor cascade (21, 22 and 23), which cascade consisted of three similar reactors. The remaining bromine required for the complete tetrabromination was fed to the first reactor of said cascade (21) at a constant rate of about 0.15 g/min simultaneously with the effluent of reactor 11. The reaction temperature in the cascade of reactors (21, 22 and 23) was 38-40° C. The total volume of the reaction mixture in said cascade was controlled at 160 ml by the simultaneous removal of the final solution. The average residence time in the cascade of reactors 21, 22 and 23 was about 15 min. After 1.5 h of continuous operation the effluent from said cascade stabilized at a solute composition of 0.2-0.3% tribromophenol, 0.5-1.5% tribromobisphenol A, and 97.5-99.2% TBBA. Reactor 11 and the cascade of reactors 21, 22 and 23 were operated with continuous addition of reagents and removal of reaction mixture for 6 h.

The productivity of all four reactors was calculated at about 0.28 g TBBA per ml reactor volume per hour during the steady continuous operation.

The bromine feed rate into reactor 21 was controlled to keep the color of the reaction mixture leaving the bromination stage (that is, exiting reactor 23) a strong yellow-orange. The unreacted bromine concentration in the organic phase of the final reaction mixture measured by a colorimeter (USB2000 Plug-and-Play Spectrometer) varied during the operation from 2400 to 4500 ppm.

After the composition of the effluent of the second reaction volume (provided within reactors 21, 22 and 23 according to the arrangement depicted in FIG. 1) was stabilized, the solid-free, completely brominated mixture, consisting of the organic phase and the aqueous phase was collected in a stirred vessel over a period of 4 h. During this time, aqueous 38% sodium bisulfite solution was fed into the vessel at a constant rate to reduce the unreacted bromine and traces of hydrogen peroxide.

iv) Treatment of the Reaction Mixture

The collected two-phase solid-free mixture consisting of an organic phase containing the TBBA and an aqueous phase containing inorganic salts was further treated in the batch mode. The organic phase was separated. According to the quantitative HPLC analysis the organic phase contained 0.11 wt. % tribromophenol and 23.2 wt. % TBBA.

After washing the organic phase with water (2×1500 ml), part of the dichloromethane was stripped so that the TBBA content in the slurry formed was 65-70%. The slurry was slowly cooled to 10° C., with stirring and kept at this temperature for 1 h. The solid was separated by filtration, washed with chilled dichloromethane and dried. The first crop of TBBA (586 g) was obtained in the form of a white free-flowing powder with a melting point of 181.4° C. GC analysis showed 0.4% tribromobisphenol A and 9.9.6% TBBA. The APHA color numbers were: 15 in a 50% solution of the product in acetone and 10 in a 20% solution in 1.5 N NaOH. The ionic bromide content was 3 ppm. The particle size distribution (PSD) measured in water, by the Malvern laser diffraction method was as follows: d(0.1) 154 μm, d(0.5) 300 μm, d(0.9) 545 μm, the average particle size 327 μm.

The mother liquor remaining after the filtration and washings was treated in a similar manner to the primary organic phase. The second crop of TBBA (128 g) was obtained in the form of a white free-flowing powder with a melting point of 181.2° C. GC analysis showed 0.7% tribromobisphenol A and 99.3% TBBA. The APHA color numbers were: 20 in a 50% solution of the product in acetone and 40 in a 20% solution in 1.5 N NaOH. The ionic bromide content was 7 ppm. The PSD was as follows: d(0.1) 142 μm, d(0.5) 336 μm, d(0.9) 780 μm, the average particle size 407 μm.

The mother liquor remaining after the filtration and washings of the second crop was treated in a similar manner to the primary organic phase. The third crop (13 g) in the form of an off-white powder with a melting point of 180.0° C. was obtained. GC analysis showed 0.3% tribromophenol, 1.2% tribromobisphenol A and 98.4% TBBA.

The total amount of TBBA isolated (727 g) constituted a yield of 96.8%, based on the BPA fed in to the reaction, during four hours of the steady continuous operation.

Example 2

Preparation of Tetrabromobisphenol A in a Batch Mode

A 1 liter reactor, equipped with a mechanical stirrer, a thermometer and a reflux condenser, was charged at ambient temperature with BPA (45.66 g, 0.2 mol), MC (366 g) and aq. 52% hydrogen peroxide (8.4 g, 0.128 mol). The rest of the aq. 52% hydrogen peroxide (18.7 g, 0.286 mol) and bromine (66.2 g, 0.414 mol) pre-mixed with 22 g MC was fed in by means of peristaltic pumps simultaneously and at constant rates, over 15 min and 1 h, respectively. The bromination was maintained at reflux (39-41° C.) by the reaction heat. About 15 min after completion of the bromine introduction a sodium bisulfite-sodium sulfite solution was added to reduce the unreacted bromine. The final bromination mixture consisted of two phases and was free from solids.

The subsequent work-up procedure for crystallizing the product and isolating the same was carried out similarly to that described for the continuous process in Example 1.

Example 3 (Comparative)

The bromination of BPA was carried out in a batch mode using a pre-prepared 23.3% slurry of BPA in dichloromethane (w/w) which corresponds to a calculated concentration of TBBA in the organic phase of the final reaction mass of about 42% by weight.

A 1 liter reactor, equipped with a mechanical stirrer, a thermometer and a reflux condenser, was charged at ambient temperature with 391.4 g of a 23.3% (w/w) slurry of BPA in dichloromethane (0.4 mol BPA) and 53.6 g aq. 52% hydrogen peroxide (0.82 mol). Bromine (132.4 g, 0.828 mol) was added to the reactor contents over 1 h. The bromination mixture was maintained at reflux (39-41° C.) by the reaction heat. About 60% of the TBBA formed precipitated during the bromination. 15 min after completion of the bromine introduction the sodium bisulfite solution was added to reduce the unreacted bromine. A further 430 g of dichloromethane was added to the slurry to give a two-phase mixture free of solids. According to the quantitative HPLC analysis the organic phase contained 0.3 wt. % tribromophenol and 22.7 wt. % TBBA. After separation, the organic phase was treated in a similar manner to that described in Example 1. The first crop of TBBA (163.2 g) was obtained in the form of a white free-flowing powder with a melting point of 181.3° C. GC analysis showed 0.5% tribromobisphenol A and 99.5% TBBA. The APHA color numbers were: 15 in a 50% solution in acetone and 20 in a 20% solution in 1.5 N NaOH. The ionic bromide content was 5 ppm. The PSD was as follows: d(0.1) 142 μm, d(0.5) 271 μm, d(0.9) 503 μm, average particle size 271 μm.

The second crop (31 g) in the form of a white free flowing powder had a melting point of 181.1° C. GC analysis showed 0.7% tribromobisphenol A and 99.3% TBBA. The APHA color numbers were: 30 in a 50% solution in acetone and 70 in a 20% solution in 1.5 N NaOH. The ionic bromide content was 8 ppm. The PSD was as follows: d(0.1) 141 μm, d(0.5) 326 μm, d(0.9) 610 μm. The third crop (7.9 g) of TBBA in the form of a yellowish powder contained 1.3% tribromobisphenol A, 98.3% TBBA with the balance being brominated phenols (GC area).

The total amount of TBBA isolated (202.1 g) constituted a yield of 92.9% based on the BPA. It is clear that carrying out the bromination with a relatively small amount of dichloromethane, corresponding to a calculated concentration of TBBA in the final organic phase of about 42% (compared to less than 25% according to the process of the invention) significantly reduces the volumetric ratio of the organic phase to the aqueous phase. The inventors theorize that since more bromine goes into the aqueous phase the formation of hypobromous acid increases, and results finally in increased decomposition of the TBBA and other brominated bisphenol A's with the formation of relatively large amounts of tribromophenol and other brominated phenols.

Example 4 (Comparative)

The bromination of BPA was carried out in a batch mode using a pre-prepared 15.2% slurry of BPA in dichloromethane which corresponds to a calculated concentration of TBBA in the organic phase of the final reaction mass, of about 30% by weight.

A 1 liter reactor, equipped with a mechanical stirrer, a thermometer and a reflux condenser, was charged at ambient temperature with 600 g of the 15.2% (w/w) slurry of BPA in dichloromethane (0.4 mol BPA) and 53.6 g aq. 52% hydrogen peroxide (0.82 mol). Bromine (132.4 g, 0.828 mol) was added to the reactor contents over 1 h. The bromination mixture was maintained at reflux (39-41° C.) by the reaction heat. After all the bromine had been fed in, 15 more minutes were required to complete the bromination. Sodium sulfite solution was added to reduce the unreacted bromine and traces of the hydrogen peroxide. Precipitation of the TBBA started within minutes to give a suspension containing a considerable amount of solid TBBA. The suspension was filtered at ambient temperature, then the cake was washed with hot water (2×200 ml). The first crop (87 g) of a fine white powder was obtained, with a poor flowability and a melting point of 181.7° C. GC analysis showed 0.4% tribromobisphenol A and 99.6% TBBA. The APHA color number of a 20% solution in 1.5 N NaOH was 170. The ionic bromide content was 52 ppm. The PSD was as follows: d(0.1) 2 μm, d(0.5) 26 μm, d(0.9) 93 μm, the average particle size 36 μm. This poor quality product constituted about 40% of all the TBBA formed.

The organic phase was washed with water and crystallized in a similar manner to that described in the working Examples. The second crop of TBBA (114.9 g) in the form of a white free flowing powder was obtained with a melting point of 181.1° C. GC analysis showed 0.5% tribromobisphenol A and 99.5% TBBA. The APHA color numbers were: 20 in a 50% solution of the product in acetone and 70 in a 20% solution in 1.5 N NaOH. The ionic bromide content was 6 ppm. The PSD was as follows: d(0.1) 135 μm, d(0.5) 290 μm, d(0.9) 490 μm. The third crop (5 g) of TBBA in the form of a yellowish powder contained 1.2% tribromobisphenol A and 98.4% TBBA with the balance being brominated phenols (GC area). The total amount of TBBA isolated (206.9 g) constituted a yield of 95.1% based on the BPA.

This example illustrates the disadvantage associated with carrying out the bromination with an amount of dichloromethane that is not sufficiently large to prevent the spontaneous precipitation of TBBA from the final reaction mixture. It was found that the product which precipitated under these conditions cannot be efficiently purified of inorganic bromides and color bodies included in the TBBA crystals. Moreover, due to the spontaneous precipitation in the presence of the aqueous phase, the product (first crop) consisted of very small particles and had poor flowability. The specified particle size and particle size distribution could not be obtained.

The results obtained in the Examples are summarized below.

TABLE 1

Effect of the amount of dichloromethane on the process

| Example | Calculated concentration of TBBA in the final organic phase, % | Tri-bromophenol formed, g/100 g TBBA formed | Yield of TBBA, based on the BPA fed, % | | | |
|---|---|---|---|---|---|---|
| | | | Crop 1 | Crop 2 | Crop 3 | Total |
| 1 | 23 | 0.47 | 78.2 | 16.9 | 1.7 | 96.8 |
| 3 Comparative | 42 | 1.3 | 75.6 | 14.3 | 3 | 92.9 |
| 4 Comparative | 30 | 0.7 | *40.0 | 52.8 | 2.3 | 95.1 |

*Precipitated spontaneously from the final reaction mixture

TABLE 2

Some characteristics of the products prepared

| Example | Crop | TBBA content, GC area % | Melting point, ° C. | Br⁻, ppm | APHA 50% acetone | APHA 20% (1.5N NaOH) | PSD, Malvern (Vol under %) vs particle size (μm) | | |
|---|---|---|---|---|---|---|---|---|---|
| | | | | | | | d(0.1) | d(0.5) | d(0.9) |
| Example 1 | 1 | 99.6 | 181.4 | 3 | 15 | 10 | 154 | 300 | 545 |
| | 2 | 99.3 | 181.2 | 7 | 20 | 40 | 142 | 336 | 780 |
| | 3 | 98.4 | 180.0 | — | — | — | — | — | — |
| 3 Comparative | 1 | 99.5 | 181.3 | 5 | 15 | 20 | 142 | 271 | 503 |
| | 2 | 99.3 | 181.1 | 8 | 30 | 70 | 141 | 326 | 610 |
| | 3 | 98.3 | — | — | — | — | — | — | — |
| 4 Comparative | 1 | 99.6 | 181.7 | 52 | — | 170 | 2 | 26 | 93 |
| | 2 | 99.5 | 181.1 | 6 | 20 | 70 | 135 | 290 | 490 |
| | 3 | 98.4 | — | — | — | — | — | — | — |

The invention claimed is:

1. A process for preparing tetrabromobisphenol A, which process comprises:
   i) reacting bisphenol A and bromine in dichloromethane in the presence of aqueous hydrogen peroxide at a temperature in the range of room temperature to the reflux temperature, wherein said dichloromethane is present in an amount sufficient for substantially dissolving brominated derivatives of said bisphenol A formed thereby,
   ii) separating the substantially solid-free reaction mixture obtained in step i) into aqueous and organic phases, precipitating tetrabromobisphenol A from the organic phase and isolating said precipitated tetrabromobisphenol A from said organic phase.

2. A process according to claim 1, wherein the bromination reaction is carried out at a temperature in the range of 30° C. to reflux temperature.

3. A process according to claim 1, wherein the volumetric ratio between the organic and aqueous phases is not less than 6:1.

4. A process according to claim 1, wherein the concentration of tetrabromobisphenol A in the organic phase is in the range of 15 to 25% by weight.

5. A process according to claim 1, wherein the substantially solid-free reaction mixture obtained in step (i) is treated with a reducing agent to reduce unreacted bromine and traces of hydrogen peroxide, and is subsequently separated into an aqueous phase and an organic phase.

6. A process according to claim 5, wherein the reducing agent is selected from the group consisting of sodium bisulfite, sodium sulfite and hydrazine.

7. A process according to claim 5, which further comprises washing the separated organic phase with water, to obtain a washed organic phase in the form of a dichloromethane solution containing substantially all the tetrabromobisphenol A as a solute, following which tetrabromobisphenol A is caused to precipitate from said washed organic phase.

8. A process according to claim 7, wherein tetrabromobisphenol A is caused to precipitate from the washed organic phase by evaporating a portion of the dichloromethane solvent to form a suspension, cooling the suspension and separating the crystals from the liquid phase.

9. A process according to claim 1, wherein the bromination reaction is carried out either in a batch mode or in a continuous mode or a combination thereof.

10. A process according to claim 9, which comprises:
    i) continuously feeding into a first reaction volume bisphenol A and bromine, reacting the same in dichloromethane in the presence of aqueous hydrogen peroxide at a temperature in the range of room temperature to the reflux temperature, wherein said dichloromethane is used in an amount sufficient for substantially dissolving brominated derivatives of said bisphenol A formed thereby, continuously removing from said first reaction volume a substantially solid-free reaction mass, contacting, in a second reaction volume, said reaction mass with bromine, to form a substantially solid-free final reaction mixture the predominate product of which is tetrabromobisphenol A;
    ii) separating said substantially solid-free final reaction mixture into aqueous and organic phases, precipitating said tetrabromobisphenol A from said organic phase and isolating the precipitated tetrabromobisphenol A from said organic phase.

11. A process according to claim 10, wherein the amount of bromine charged into the first reaction volume is 80 to 95% of the total amount of bromine used in the bromination reaction.

12. A process according to claim 10, wherein the solid-free organic phase at the end of the bromination reaction contains 1000 to 10,000 ppm unreacted bromine.

13. A process according to claim 10, wherein the first reaction volume is provided in a first continuous reactor and the second reaction volume is provided within at least two consecutively arranged continuous reactors, wherein the reaction mass exiting said first reactor and bromine are continuously fed into the first of said at least two consecutively arranged reactors.

14. A process according to claim 10, wherein the substantially solid-free reaction mixture obtained in step (i) is treated with a reducing agent to reduce unreacted bromine and traces of hydrogen peroxide, and is subsequently separated into an aqueous phase and an organic phase.

15. A process according to claim 14, which further comprises washing the separated organic phase with water, to obtain a washed organic phase in the form of a dichloromethane solution containing substantially all the tetrabromobisphenol A as a solute, following which tetrabromobisphenol A is caused to precipitate from said washed organic phase.

16. A process according to claim 15, wherein tetrabromobisphenol A is caused to precipitate from the washed organic phase by evaporating a portion of the dichloromethane solvent to form a suspension, cooling the suspension and separating the tetrabromobisphenol A crystals from the liquid phase.

17. A process according to claim 10, wherein the content of the tribromophenol in the final bromination mixture is less than 0.6% (GC area %) relative to the tetrabromobisphenol A.

18. A process according to claim 1, wherein the tetrabromobisphenol A obtained has one or more of the following characteristics:
   (i) a purity of at least 99% (gas chromatography area);
   (ii) ionic bromide content of less than 10 ppm;
   (iii) APHA color number of a 50% solution in acetone less than 30; and
   (iv) APHA color number of a 20% solution in 1.5 N sodium hydroxide of less than 70
   (v) Melting point higher than 180° C.

* * * * *